United States Patent
Tseng

(10) Patent No.: US 6,398,381 B1
(45) Date of Patent: Jun. 4, 2002

(54) WIND-DRIVEN PERFUME DISPENSER CAPABLE OF PRODUCING DIFFERENT LIGHT PATTERNS

(76) Inventor: Wen Yung Tseng, PO Box 82-144, Taipei (TW)

(*) Notice: Subject to any disclaimer, the term of this patent is extended or adjusted under 35 U.S.C. 154(b) by 1 days.

(21) Appl. No.: 09/618,476

(22) Filed: Jul. 18, 2000

(51) Int. Cl.$^7$ .............................................. F21V 33/00
(52) U.S. Cl. ..................... 362/96; 362/234; 362/253; 362/276; 362/800; 362/802; 362/806
(58) Field of Search .................... 362/276, 96, 124, 362/545, 234, 253, 800, 806, 808, 802; 40/441; 422/121, 124

(56) References Cited

U.S. PATENT DOCUMENTS 6,050,551 A * 4/2000 Anderson ............... 422/124 X
6,086,214 A * 7/2000 Ridge ........................ 362/96
6,103,201 A * 8/2000 Green ....................... 422/124
6,193,384 B1 * 2/2001 Stein ......................... 362/96

* cited by examiner

Primary Examiner—Stephen Husar
(74) Attorney, Agent, or Firm—A & J

(57) ABSTRACT

A wind-driven perfume dispenser capable of producing different light patterns includes a body portion, a rotatable light-emitting device rotatably mounted on the body portion, and a decoration, the rotatable light-emitting device including an impeller and a light-emitting device mounted on the impeller, whereby the light-emitting device will give light when the impeller is blown by wind and, almost at the same time, the integrated circuit will control the light-emitting diodes to give various kinds of light patterns which will pass through the opening of the decoration to produce a mysterious and appealing appearance, especially at night time.

13 Claims, 2 Drawing Sheets

WIND-DRIVEN PERFUME DISPENSER CAPABLE OF PRODUCING DIFFERENT LIGHT PATTERNS

BACKGROUND OF THE INVENTION

1. Field of the Invention

This invention is related to a wind-driven perfume dispenser and in particular to one which will produce different light patterns when blown by the wind.

2. Description of the Prior Art

A variety of perfume dispensers have have appeared on the market, which have been utilised in offices, houses, motor vehicles, etc., for dispensing a perfume. These perfume dispensers are commonly comprised of a perfume container having air vents, and a solid or liquid perfume contained in the perfume container. However, the perfume dispensers are less active and the smell of the perfume used cannot be quickly and effectively distributed into the air. Furthermore, such perfume dispensers have no other functions than dispensing the smell of the perfume thereby making it difficult to attract the purchasing desire of the customers.

Therefore, it is an object of the present invention to provide a wind-driven perfume dispenser which will produce different light patterns when blown by wind, which can obviate and mitigate the above-mentioned drawbacks.

SUMMARY OF THE INVENTION

This invention is related to a wind-driven perfume dispenser.

It is the primary object of the present invention to provide a wind-driven perfume dispenser which will produce different light patterns when blown by wine According to a preferred embodiment of the present invention, a wind-driven perfume dispenser capable of producing different light patterns includes a body portion, a rotatable light-emitting device rotatably mounted on the body portion, and a decoration. The rotatable light-emitting device includes an impeller and a light-emitting device mounted on the impeller, whereby the light-emitting device will give light when the impeller is blown by wind, and almost at the same time, the integrated circuit will control the light-emitting diodes to give various kinds of flashing modes which will pass through the opening of the decoration to produce a mysterious and appealing appearance, especially at night time.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts. Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENT

Figure 1:
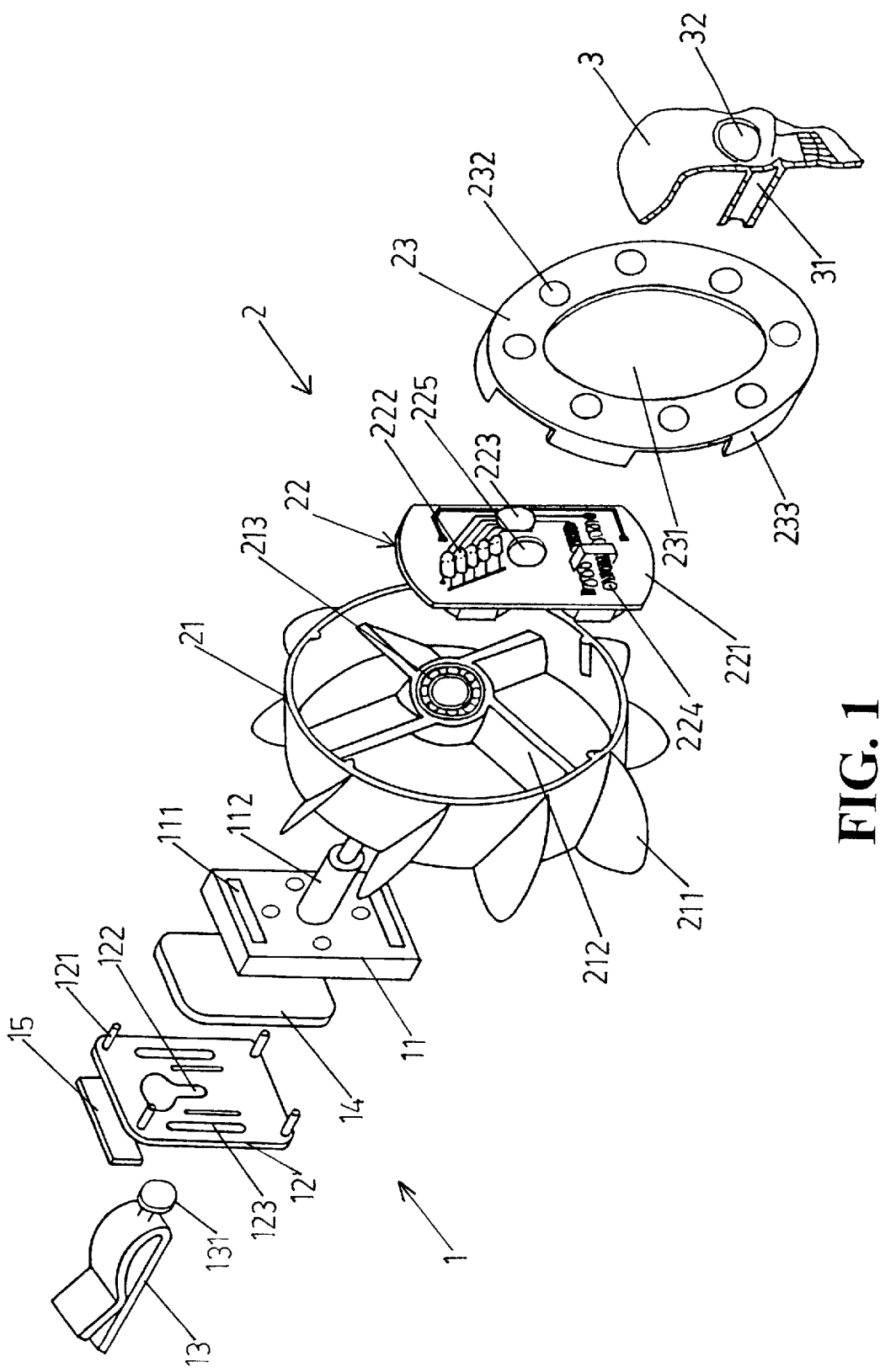
FIG. 1 is an exploded view of the present invention.
Figure 2:
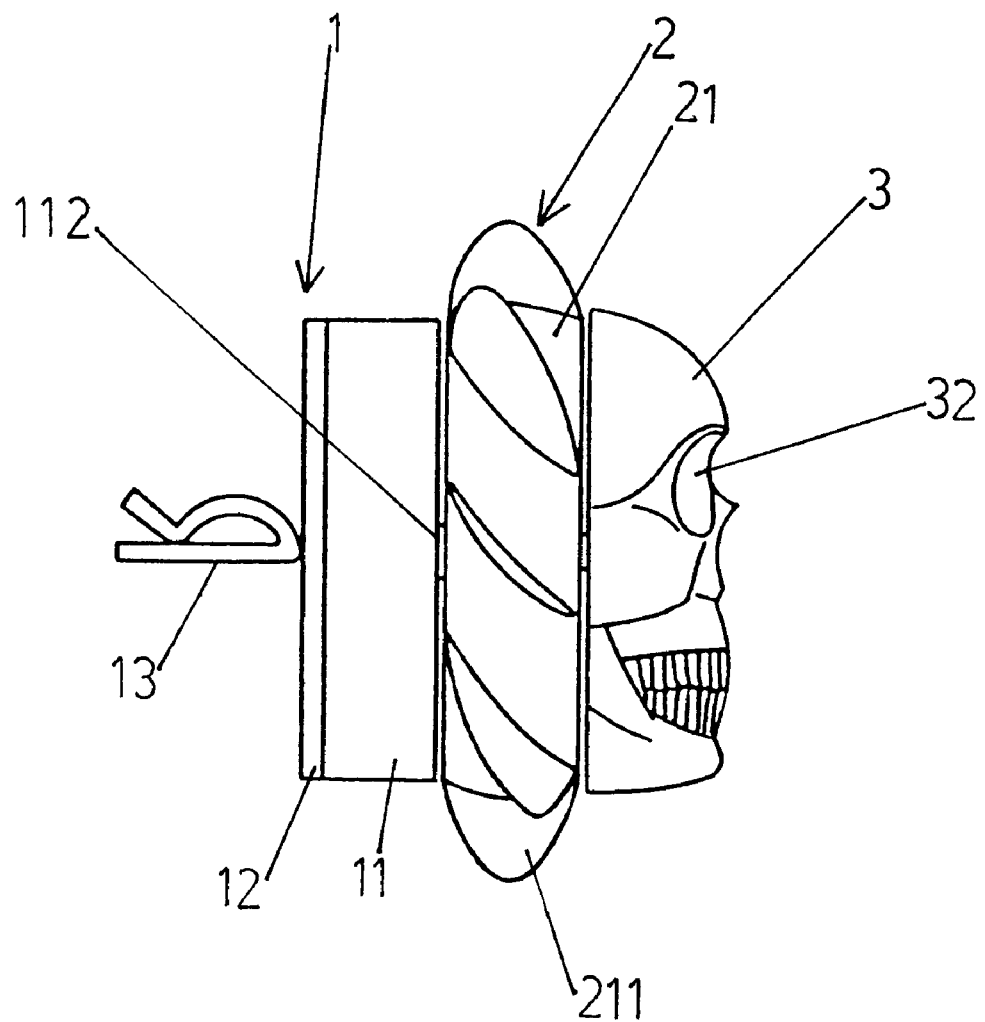
FIG. 2 is a side view of the present invention.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

With reference to the drawings and in particular to FIG. 1 thereof, the present invention generally comprises a body portion 1, a rotatable light-emitting device 2 and a decoration 3. The body portion 1 includes a rectangular casing 11, a cover 12 and a clip 13. The rotatable light-emitting device 2 includes an impeller 21, a light-emitting member 22 and a covering plate 23. The rectangular casing 11 has an open side and has a slot 111 for air ventilation and a rod 112 at the center of the front side thereof. A perfume emitter 14 is arranged inside the rectangular casing 11. The cover 12 has four pins 121 adapted to be inserted into corresponding holes (not shown) of the rectangular member 11 so as to close the rectangular casing 11 thereby keeping the perfume emitter 14 therein. The cover 12 is formed with a key hole 122 configured to engage with a head 131 of the clip 13 so that the clip 13 can be fixedly engaged with the cover 12. In addition, the cover 12 is formed with slots 123 for air ventilation. The impeller 21 has a cylindrical body with a center formed with a through hole in which is fitted a bearing 213. The impeller 21 is provided with a plurality of blades 211 extending outwardly from the outer side cylindrical body and a plurality of ribs 212 extending from the center to the inner side of the cylindrical body. The rectangular casing 11 is mounted on the impeller 21, with the rod 112 of the former engaging with the bearing 213 of the latter, so that the impeller 21 can be freely rotated with respect to the rectangular casing 11. The light-emitting device 22 includes a printed circuit board 221 on which are mounted a plurality of light-emitting diodes 222 with the same or different colors, an integrated circuit 223, a rotation sensor 224 and batteries. The printed circuit board 221 has a center hole 225 and arranged on the other side of the impeller 21 with the rod 112 of the rectangular casing 11 extending trough the center hole 225 of the printed circuit board 221. The rotation sensor 224 is a spring member so that when the printed circuit board 221 is rotated, the length of the spring member will vary with the centrifugal force thereby causing changes in the electrical circuit. As the integrated circuit 223 detects the changes, it will send out a signal to cause the light-emitting diodes 222 to give light. The number of the light-emitted diodes which will give light and the time period that the light-emitted diodes will give light are controlled by the integrated circuit 223 thus causing a variety of changes. The covering plate 23 is an annular member having an opening 231 at the center, a plurality of holes 232 at the circumference, and a plurality of lugs 233 extending from the circumference. The covering plate 23 is engaged with the impeller 21, with the lugs 233 of the former bearing against the inner side of the cylindrical body of the latter. The decoration 3 has a tubular member 31 extending from one side thereof and is mounted on the covering plate 23 with the tubular member 31 extending through the opening 31 of the covering plate 23 and the center hole 225 of the printed circuit board 22 to snugly engage with the rod 112 of the rectangular casing 11. The decoration 3 has an opening 32 for the passage of the light given by the light-emitting diodes 222.

When desired to mount the present invention in a car, it is only necessary to engage the clip 13 of the present invention with the outlet of the air conditioner or affix the present invention to the outlet of the air condition by double-sided adhesive tape, so that when air comes out of the outlet of the air conditioner, the impeller 21 will be rotated thereby rotating the light-emitting device 22. In the meantime, the integrated circuit 223 will control the light-emitting diodes 222 to give various kinds of flashing modes which will pass through the opening 32 of the decoration 3 to produce a mysterious and appealing appearance, especially at night time.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A wind-driven perfume dispenser capable of producing different light patterns comprising a body portion, a rotatable light-emitting device rotatably mounted on said body portion, and a decoration, said rotatable light-emitting device including an impeller and a light-emitting device mounted on said impeller, whereby said light-emitting device will give light when said impeller is blown by wind.

2. The wind-driven perfume dispenser capable of producing different light patterns as claimed in claim 1, wherein said body portion includes a rectangular casing and a cover engageable with said rectangular casing.

3. The wind-driven perfume dispenser capable of producing different light patterns as claimed in claim 2, wherein an outer side of id cover is engaged with a clip.

4. The wind-driven perfume dispenser capable of producing different light patterns as claimed in claim 2, wherein said rectangular casing contains a perfume emitter therein.

5. The wind-driven perfume dispenser capable of producing different light patterns as claimed in claim 2, wherein said impeller has a cylindrical body having a center formed with a through hole in which is fitted a bearing for receiving a rod of said rectangular casing, a plurality of blades extending outwardly from an outer side of said cylindrical body, and a plurality of ribs extending from a center to an inner side of said cylindrical body.

6. The wind-driven perfume dispenser capable of producing different light patterns as claimed in claim 2, wherein rotatable light-emitting device includes a printed circuit board, a plurality of light-emitting diodes, an integrated circuit, a rotation sensor and batteries.

7. The wind-driven perfume dispenser capable of producing different light patterns as claimed in claim 6, wherein said light-emitting diodes are of same or different colors.

8. The wind-driven perfume dispenser capable of producing different light patterns as claimed in claim 6, wherein said printed circuit board has a hole for passage of a rod of said rectangular casing.

9. The wind-driven perfume dispenser capable of producing different light patterns as claimed in claim 6, wherein said printed circuit board is mounted on an inner side of said impeller.

10. The wind-driven perfume dispenser capable of producing different light pattern as claimed in claim 9, wherein said impeller is engaged with a covering plate at an inner side thereof for fixing said printed circuit in place.

11. The wind-driven perfume dispenser capable of producing different light patterns as claimed in claim 10, wherein said covering plate is an annular member having an opening at a center thereof, a plurality of holes at a circumference thereof and a plurality of lugs extending from the circumference for bearing against the inner side of said impeller.

12. The wind-driven perfume dispenser capable of producing different light patterns as claimed in claim 8, wherein said decoration has a tubular member extending from one side thereof and is mounted on said covering plate with said tubular member engaged with said rod of said rectangular casing.

13. The wind-driven perfume dispenser capable of producing different light patterns as claimed in claim 6, wherein said decoration has an opening for passage of light given by said light-emitting diodes.

* * * * *